United States Patent
Haldar et al.

(10) Patent No.: US 8,168,219 B2
(45) Date of Patent: May 1, 2012

(54) SYNERGISTIC BINDER COMPOSITION, METHOD FOR MAKING SAME, AND TABLETS OF AN ACTIVE AND SAID BINDER HAVING ADVANTAGEOUS HARDNESS AND FRIABILITY

(75) Inventors: Rama Haldar, Randolph, NJ (US); Dipan B. Ray, Old Bridge, NJ (US); Timothy G. Bee, North Plainfield, NJ (US); Sidney Etienne, Ridgefield Park, NJ (US); Su-Jane Cheng, Taipie Hsien (TW)

(73) Assignee: ISP Investments Inc., Wilmington, DE (US)

( * ) Notice: Subject to any disclaimer, the term of this patent is extended or adjusted under 35 U.S.C. 154(b) by 1689 days.

(21) Appl. No.: 11/290,715

(22) Filed: Nov. 30, 2005

(65) Prior Publication Data

US 2007/0122472 A1    May 31, 2007

(51) Int. Cl.
 *A61K 9/20* (2006.01)
(52) U.S. Cl. ..................................... 424/464
(58) Field of Classification Search ............ None
See application file for complete search history.

(56) References Cited

U.S. PATENT DOCUMENTS 5,490,990 A * 2/1996 Grabowski et al. ........... 424/486
6,066,334 A 5/2000 Kolter et al.
6,099,863 A * 8/2000 Gilis et al. .................... 424/475

OTHER PUBLICATIONS

Moroni, A., "A Novel Copovidone Binder for Dry Granulation and Direct-Compression Tableting," *Pharmaceutical Technology Drug Delivery*, vol. 24, pp. 8-12, (Sep. 2001).

\* cited by examiner

*Primary Examiner* — Tracy Vivlemore
*Assistant Examiner* — Jennifer Berrios
(74) *Attorney, Agent, or Firm* — Thompson Hine LLP; William J. Davis; Walter Katz

(57) ABSTRACT

Tablets of a pharmaceutical, nutritional or vitamin active compound or composition, e.g. a poorly compressible drug are made by direct compression using a synergistic binder composition of co-processed (a) copolymer of vinylpyrrolidone (VP) and vinyl acetate (VA) and (b) microcrystalline cellulose (MCC), in a wt. ratio of (a):(b) of 1-30:99-70, which is spray dried to provide a readily compressible excipient binder powder for such active. The tablets obtained herein have advantageous hardness and friability at an acceptable compression force.

17 Claims, No Drawings

SYNERGISTIC BINDER COMPOSITION, METHOD FOR MAKING SAME, AND TABLETS OF AN ACTIVE AND SAID BINDER HAVING ADVANTAGEOUS HARDNESS AND FRIABILITY

BACKGROUND OF THE INVENTION

1. Field of the Invention

This invention relates to tableting of pharmaceutical, nutritional or vitamin active compounds or compositions, e.g. a poorly compressible drug, and, more particularly, to a new and improved synergistic binder composition and method for making the same, and to processing such actives and binder into tablets of advantageous hardness and friability by direct compression at a suitable compression force.

2. Description of the Prior Art

Many commercial filler materials such as microcrystalline cellulose and silicified microcrystalline cellulose are used in the manufacture of tablets of pharmaceutical, nutritional and vitamin active compounds and compositions. Such materials are described by Tobyn, M. J. in Int. J. of Pharmaceutics, 169, 183-194 (1998). However, actives such as drugs which are difficult to compress require tableting machines which operate at high compression forces to provide tablets of suitable hardness and low friability. Also, large amounts of the filler may be necessary to achieve these results, which, disadvantageously, increases the size of the tablet.

A. Moroni, et al., in U.S. Pat. No. 6,524,617, described a synergistic binder composition for making pharmaceutical tablets of suitable hardness at low compression force, and low friability, which precluded damage to the tablet upon further processing, and without requiring a substantial increase in the size of the tablet. The Moroni composition included a VP-VA copolymer and microcrystalline cellulose.

Accordingly, it is an object of this invention to provide an improved synergistic binder composition, and method of making the same, for forming tablets of a pharmaceutical, nutritional or vitamin compound or composition, e.g. a poorly compressible drug, by direct compression at a low compression force, which provides tablets having advantageous hardness and low friability.

SUMMARY OF THE INVENTION

Tablets of a pharmaceutical, nutritional or vitamin active compound or compositions, e.g. a poorly compressible drug, are made herein by direct compression using a binder composition of a co-processed copolymer of (a) vinylpyrrolidone (VP) and vinyl acetate (VA), in a suitable wt. ratio of 30-90: 70-10, and microcrystalline cellulose (MCC), in a wt. ratio of (a):(b) 1-30:99-70. The invention composition, in the form of an aqueous dispersion, is spray dried at predetermined temperatures and spray rate to provide an excipient binder powder with a desired particle size for such actives. The tablets obtained herein have advantageous hardness and friability, and are processed at an acceptable compression force.

The preferred copolymer in the binder composition of the invention is VP and VA, at a wt. ratio of about 60 wt. % VP and about 40 wt. % VA.

The most preferred binder composition is VP-VA and MCC in a wt. ratio of about 10:90.

In the process of making the binder composition of the invention, an aqueous dispersion of copolymer VP-VA (PLASDONE® S-630), (International Specialty Products, Inc.) and microcrystalline cellulose, are spray dried under predetermined temperatures and spray rate conditions to produce a binder powder particularly suitable for direct compression of such actives, including poorly compressible drug actives. Preferably spray drying is carried out at an inlet temperature of about 200°-300° C. and an outlet temperature of about 75-95° C. at a rotary atomizer speed rate of about 12,000 to 24,000 rpm.

Pharmaceutical tablets made by the invention generally include, by wt., 1-85% of an active which may be a poorly compressible drug and 99-15% of the invention co-processed binder powder. Suitably, such drug tablets have a hardness of at least 6 kP and a friability of <2%.

Tablets are made by direct compression of the binder powders and the active, and, optionally, other excipients typically present in such formulations. Direct compression of the formulation at about 2000 to 7000 lbs provides a tablet having a hardness of about 6-20 kP and a friability of about 1-2%.

DETAILED DESCRIPTION OF THE INVENTION

Suitable pharmaceutical nutritional and vitamin actives include those described by Doney in Provisional U.S. Patent Application Ser. No. 60/703,374, filed Jul. 28, 2005 the disclosure of which is hereby incorporated by reference.

The invention will now be illustrated in more detail by reference to the following examples.

EXAMPLE 1

An aqueous dispersion of a binder composition of VP-VA copolymer (60:40 by wt.) and MCC, in a wt. ratio of 1-30: 99:70, and a solids content of about 15-30%, were spray dried in a laboratory scale disc or nozzle spray dryer at an inlet temperature of 200-300° C. and an outlet temperature of 75-95° C., at an atomizer speed rate of 12,000-24,000 rpm. Powders of a free-flowing binder composition were collected. The powders had a mean particle size of about 20-120μ.

EXAMPLE 2

The free-flowing binder powders obtained in Example 1 were admixed with a poorly compressible drug (acetaminophen) at a wt. ratio of 50:20 drug:binder with the remainder of the formulation being comprised of filler (27%), a disintegrant (2%), a glidant (0.5%), and a lubricant (0.5%). Formulations of the spray dried binder composition and drug ready for direct compression into tablets are given in Table 1 below. Runs 1-3 for such formulations were made using spray dried powders of VP-VA (PLASDONE® S-630) and MCC, at various wt. ratios, while runs 4-5 (controls) were made using only physical blends of these materials. The results in Table 2 show that the invention runs 1-3 had a substantially increased tablet hardness and decreased friability as compared to control runs 4-5.

TABLE 1

Drug Formulations of Invention and Controls

| | Spray Dried Powder* (Invention) | | | Physical Blend + (Control) | |
|---|---|---|---|---|---|
| | Formulation Nos. | | | | |
| Ingredient | 1 | 2 | 3 | 4 | 5 |
| Acetaminophen (drug) | 50.00 | 50.00 | 50.00 | 50.00 | 50.00 |
| Fast-Flow Lactose (filler) | 27.00 | 27.00 | 27.00 | 27.00 | 27.00 |
| S-630/MCC [5/95]* (binder) | 20.00 | — | — | — | — |

TABLE 1-continued

Drug Formulations of Invention and Controls

| | Spray Dried Powder* (Invention) | | | Physical Blend + (Control) | |
|---|---|---|---|---|---|
| | Formulation Nos. | | | | |
| Ingredient | 1 | 2 | 3 | 4 | 5 |
| S-630/MCC [10/90]* (binder) | — | 20.00 | — | — | — |
| S-630/MCC [15/85]* (binder) | — | — | 20.00 | — | — |
| S-630/MCC [5/95]+ (binder) | — | — | — | 20.00 | — |
| S-630/MCC [10/90]+ (binder) | — | — | — | — | 20.00 |
| POLYPLASDONE XL (disintegrant) | 2.00 | 2.00 | 2.00 | 2.00 | 2.00 |
| CAB-O-SIL ® HS-5 (glidant) | 0.50 | 0.50 | 0.50 | 0.50 | 0.50 |
| Magnesium Stearate (lubricant) | 0.50 | 0.50 | 0.50 | 0.50 | 0.50 |
| Total | 100.00 | 100.00 | 100.00 | 100.00 | 100.00 |

TABLE 2

Physical Properties of Drug Tablets of Formulations of Table 1

| | 1 | 2 | 3 | 4 | 5 |
|---|---|---|---|---|---|
| 3,000 lbs. C.F. | | | | | |
| Compression Force (lbs.) | 3057.42 | 2945.01 | 3034.94 | 2967.49 | 2989.97 |
| Tablet Weight (mg) | 351.21 | 354.17 | 349.86 | 356.69 | 357.56 |
| Tablet Hardness (kP) | 8.90 | 10.95 | 10.22 | 7.65 | 8.18 |
| Disintegration (min:sec) | 0' 13" | 0' 13" | 0' 13" | — | — |
| Friability (% Loss) | 0.78 | 0.55 | 0.50 | 1.49 | 1.29 |
| 5,000 lbs. C.F. | | | | | |
| Compression Force (lbs.) | 5013.26 | 5013.26 | 4945.82 | 4990.78 | 4923.34 |
| Tablet Weight (mg) | 359.85 | 355.14 | 352.89 | 364.59 | 357.65 |
| Tablet Hardness (kP) | 11.82 | 13.10 | 12.82 | 8.53 | 10.93 |
| Disintegration (min:sec) | 0' 15" | 0' 15" | 0' 15" | — | — |
| Friability (% Loss) | 0.68 | 0.60 | 0.51 | 1.18 | 1.14 |
| 7,000 lbs. C.F. | | | | | |
| Compression Force (lbs.) | 7036.55 | 6991.59 | 6991.59 | 6991.59 | 7014.07 |
| Tablet Weight (mg) | 351.33 | 356.83 | 352.10 | 359.03 | 358.78 |
| Tablet Hardness (kP) | 13.17 | 13.78 | 14.17 | 8.98 | 9.27 |
| Disintegration (min:sec) | 0' 20" | 0' 28" | 0' 33" | — | — |
| Friability (% Loss) | 0.50 | 0.49 | 0.41 | 1.09 | 0.82 |

While the invention has been described with particular reference to certain embodiments thereof, it will be understood that changes and modifications may be made which are within the skill of the art. Accordingly, it is intended to be bound only by the following claims, in which:

What is claimed is:

1. A process for making tablets of a pharmaceutical, nutritional or vitamin active compound or composition by direct compression, which comprises providing an aqueous dispersion of (a) a copolymer of vinylpyrrolidone (VP) and vinyl acetate (VA) and (b) microcrystalline cellulose (MCC), in a wt. ratio of (a) to (b) of 1-30:99-70, spray drying said aqueous dispersion to form powders thereof, admixing said powders and said active, and forming a tablet thereof by direct compression.

2. A process according to claim 1 wherein (a) has a wt. ratio of 30-90 VP and 70-10 VA.

3. A process according to claim 1 wherein said copolymer comprises about 60 wt. % VP and about 40% wt. VA.

4. A process according to claim 1 wherein the binder powders have an average particle size of about 20-120 μ (0.79-4.72 mils).

5. A process according to claim 1 wherein said active is present in said tablet in an amount of 1-85 wt. % and said binder composition is present in an amount of 99-15 wt. %.

6. A process according to claim 1 wherein direct compression is carried out at 2000-7000 lbs. (8.9-31.1 kN) and the tablet has a hardness of at least 6 kP (59N; 13 lbf) and a friability of less than 2%.

7. A process according to claim 6 wherein said tablet hardness is about 8-30 kP (79-294N; 18-66 lbf) and said friability is about 1-2%.

8. A process according to claim 5 wherein said active is present in an amount of 50 to 70 wt. % in said mixture of binder composition and drug.

9. A process according to claim 1 in which said tablet also includes other excipients.

10. A process according to claim 1 wherein said active is a drug.

11. A free-flowing, co-processed powdered binder composition obtained by spray drying an aqueous dispersion of (a) a copolymer of VP and VA and (b) MCC, in a wt. ratio of (a):(b) of 1-30:99-70.

12. The free-flowing co-processed powdered binder composition according to claim 11 having a mean particle size of 20-120 μ (0.79-4.72 mils).

13. The free-flowing co-processed powdered binder composition according to claim 11 wherein (a) comprises 30-90% VP and 10-70% VA.

14. The free-flowing, co-processed powdered binder composition according to claim 11 wherein spray drying is carried out on an aqueous dispersion of said copolymer and MCC at an inlet temperature of about 200-300° C. (392-572° F.) and an outlet temperature of about 75-95° C. (167-203° F.), at an atomizer speed rate of about 12,000 to 24,000 rpm.

15. The free-flowing, co-processed powdered binder composition according to claim 13 wherein said copolymer comprises about 60 wt. % VP and about 40 wt. % VA.

16. The free-flowing, co-processed powdered binder composition according to claim 13 wherein the wt. ratio of (a):(b) is from about 5-15:85-95.

17. A process according to claim 3 wherein the wt. ratio of (a):(b) is from about 5-15:85-95.

* * * * *